US006416765B1

(12) United States Patent
Donovan

(10) Patent No.: US 6,416,765 B1
(45) Date of Patent: *Jul. 9, 2002

(54) NEUROTOXIN THERAPY FOR DIABETES

(75) Inventor: Stephen Donovan, Capistrano Beach, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/972,702

(22) Filed: Oct. 3, 2001

Related U.S. Application Data

(63) Continuation of application No. 09/491,420, filed on Jan. 26, 2000, now Pat. No. 6,337,075, which is a continuation-in-part of application No. 09/482,831, filed on Jan. 11, 2000, now Pat. No. 6,143,306.

(51) Int. Cl.[7] .......................... A61K 39/02; A61K 39/08
(52) U.S. Cl. .................. 424/236.1; 424/239.1; 514/866
(58) Field of Search ............................. 424/236.1, 239.1

(56) References Cited

U.S. PATENT DOCUMENTS 6,143,306 A * 11/2000 Donovan .................. 424/236.1
6,261,572 B1 * 7/2001 Donovan .................. 424/239.1

FOREIGN PATENT DOCUMENTS

| WO | WO95/17904 | 7/1995 |
| WO | WO01/51074 A1 | 7/2001 |
| WO | WO01/54711 A2 | 8/2001 |

OTHER PUBLICATIONS

Sadoul, K. et al., SNAP–23 is not cleaved by botulinum neurotoxin E and can replace SNAP–25 in the process of insulin secretion, Journal of Biological Chemistry, vol. 272, No. 52, Dec. 22, 1997, pp. 33023–33027, XP–002159204.
Regazzi, R., et al., VAMP–2 and cellubrevin are expressed in pancreatic β–cells and are essential for $Ca^2+$—but not for GTPγS–induced insulin secretion, The EMBO Journal, vol. 14, No. 12, pp. 2723–2730, 1995, XP–002182255.

Ahren, Bo, et al., Increased insulin secretion and normalization of glucose–tolerance by cholinergic agonism in high fat–fed mice, American Journal of Physiology, vol. 277, pp. E93–E102, 1999, XP–002157050.
Schmitt T., et al., *Selektive Denervierung durch Botulinus–Toxin als therapeutisches Prinzip im Gastrointestinaltract*, Deutsche Medizinische, Wochenschrift, Vo. 124, No. 7, Feb. 1999, pp. 197–203, XP–000971721.
Wehrmann, T., et al. *Endoscopic botulinum* toxin injection-into the minor papilla for treatment for treatment for idiopathic recurrent pancreatitis in patients with pancreas divisum, Gastrointestinal Endoscpoy, vol. 50, No. 4, 1999 pp. 545–548, XP–000971257.
Di Francesco, V., et al., Injection of botulinum toxin into the sphincter of oddi in patients with acute recurrent pancreatitis: 'an effective medical sphincterotomy'?, Gastroenterology, vol. 59, No. 3, May 1998, p. 231, XP–000971731.
Di Francesco, V., et al., Injection of botulin toxin into the sphincter of ODDI in patients with acute recurrent pancreatitis: an effective "medical sphincterotomy"?, Gastroenterology, vol. 114, No. 4 Part 2, Apr. 1998 pp. A453–A454, XP–002157048.
Okolo, P.I., et al., Immediate reduction of pancreatic so pressure after endoscopic injectionof botulinum toxin (BoTox): implications of prevention of ERCP–induced pancreatitis, Gastroenterology, vol. 114, No. 4, Part 2, Apr. 1998, p. A535, XP–000971724.

* cited by examiner

*Primary Examiner*—Frederick Krass
*Assistant Examiner*—Donna Jagoe
(74) *Attorney, Agent, or Firm*—Martin A. Voet; Robert J. Baran; Carlos A. Fisher

(57) ABSTRACT

The invention encompasses a method for treating hyperinsulinemic type 2 diabetes by local administration of a neurotoxin, such as a botulinum toxin, into the pancreas, thereby reducing insulin secretion from a B cell, and a method for treating hypoinsulinemic type 2 diabetes by local administration of a neurotoxin, such as a botulinum toxin, into a sympathetic ganglion, thereby reducing an inhibitory effect upon insulin secretion.

25 Claims, No Drawings

NEUROTOXIN THERAPY FOR DIABETES

CROSS REFERENCE

This application is a continuation of pending application Ser. No. 09/491,420, filed Jan. 26, 2000 now U.S. Pat. No. 6,337,075, which is a continuation in part of application Ser. No. 09/482,831, filed Jan. 11, 2000, now U.S. Pat. No. 6,143,306.

BACKGROUND

The present invention relates to methods for treating diabetes. In particular the present invention relates to methods for treating diabetes by administration of a neurotoxin to a patient.

Diabetes

The human pancreas is a gland comprised of both exocrine and endocrine tissues. The acinar cells of the exocrine pancreas secret digestive enzymes while the ductal cells of the exocrine pancreas secret an electrolyte solution.

The endocrine pancreas comprises the pancreatic islets of Langerhan which are aggregations of polypeptide hormone producing cells scattered widely throughout the acinar tissue and which are most numerous in the tail portion of the pancreas. Typically, total islet tissue constitutes only about 1 or 2 percent of the pancreatic mass.

Islet tissue contains at least three functionally different types of cells. These three cell types are A cells which can make glucagon, B (or β) cells which make insulin and D cells which can make a third islet hormone, somatostatin. The B cells are the most abundant of the three types of islet cells. Insulin promotes the uptake of glucose by cells, especially muscle cells and prevents an excessive breakdown of glycogen stored in liver and muscle. As an antidiabetic hormone essential for lowering blood sugar, insulin is a powerful hypoglycemic agent. In most instances, the actions of glucagon are contrary to those of insulin. Thus, glucagon is a hyperglycemic factor which causes blood sugar to increase.

Glucose is the major factor which promotes release of insulin from islet B cells. Glucose also reduces glucagon secretion from islet A cells. Like glucose, glucagon (from islet A cells) also promotes insulin secretion from the islet B cells.

Diabetes mellitus is the most common endocrine disorder and is a chronic condition. It is estimated that in 1999 there were 100 million people worldwide with diabetes and the number of diabetics worldwide is expected to reach 300 million within the next ten years, that is by the year 2009. *Type 2 Diabetes Prediction and Prevention*, edited by Graham A. Hitman, John Wiley & Sons publisher, preface (1999), the entire contents of which publication are incorporated herein by reference. Unfortunately, diabetic retinopathy is a leading cause of blindness and other complications of diabetes include renal disease, foot problems and neuropathic conditions. Of the major forms of diabetes mellitus, type 2 diabetes cases outnumber type 1 diabetes cases by a ratio of about ten to one.

In type 1 or insulin dependent diabetes mellitus (IDDM) the B cells of the pancreas, and hence the capacity to make insulin, are destroyed by what is probably an autoimmune disease. Insulin replacement is the preferred therapy. Whereas at most about 20% of the cases of diabetes mellitus are type 1 or IDDM, typically about 80% to 90% of the cases of diabetes mellitus are type 2 or non insulin dependent diabetes mellitus (NIDDM). Although NIDDM is more prevalent than IDDM, its pathogenesis is not well understood. It has though been determined that NIDDM is the result of both a beta cell defect and insulin resistance. Thus, patients with type 2 NIDDM have the two physiological defects of hypersecretion of insulin (during at least the early phase of type 2 diabetes) and resistance to insulin in target tissues. There is support for the belief that hyperinsulinemia is the primary defect and it is known that in the early stages of type 2 diabetes, B cell production of insulin increases. *Type 2 Diabetes Prediction and Prevention*, supra, pages 199 and 311. Thus, in the first phase (new onset) of NIDDM, the plasma glucose level is normal despite demonstrable insulin resistance with elevated insulin levels. In the second phase insulin resistance worsens so that postprandial hyperglycemia develops despite elevated insulin. In the third or late phase of type diabetes, insulin resistance does not change but declining insulin secretion causes fasting hyperglycemia and overt diabetes. It is possible that early phase hypersecretion of insulin causes the insulin resistance. Thus, the primary defect can be due to disfunctional islet cells cause insulin hypersecretion which leads to insulin resistance. In support of this theory, one can note that B cell mass is intact in type 2 NIDDM, while most beta cells have been destroyed in type 1 IDDM. Interestingly, the alpha cell population is increased in type 2 NIDDM, resulting in an elevated ratio of alpha to beta cells and excess glucagon production. *Harrison's Principles of Internal Medicine* $14^{th}$ Edition (1998), pages 2064–65.

Unfortunately, high insulin levels, such as can occur in early phase type 2 diabetes have recently been linked to an increased risk of blood clots. Thus, patients with elevated insulin also have impaired ability to dissolve blood clots (impaired fibrinolysis). Significantly, blood clot formation is a major cause of heart attack and is the cause of the most common type of stroke. *J Am Med Assoc*, 2000;283:221–228.

There is clearly therefore a need to treat hyperinsulinemia, such as can occur during, at least, the early phase of type 2 diabetes. Unfortunately, there are many drawbacks and deficiencies with known treatments for type 2 NIDDM. Thus, current therapy for type 2 NIDDM can include administration of an oral agent such as a sulfonylurea (for example acetohexamide, chlorpropamide, tolazamide, glimeripiride, glyburide or glibornuride) which acts by stimulating B cell secretion of insulin, in an attempt to overcome the insulin resistance of early phase type 2 diabetes or to address the declining insulin production by B cells in late phase, type 2 diabetes. Unfortunately, sulfonylureas increase extrapancreatic insulin receptors. Additionally, severe and prolonged hypoglycemia can follow sulfonylurea administration, which can necessitate a need for massive glucose infusions. Furthermore, oral sulfonylureas can have undesirable systemic effects. Finally, sulfonylureas typically have a duration of action of only about 12–60 hours per dose of sulfonylurea administered. Thus, a need exists for a more effective anti-diabetic drug.

Endocrine pancreatic innervation of the islets of Langerhan is through both sympathetic and parasympathetic nerve fibers which terminate on or near islet cells. Thus, sympathetic nerve fibers appear to inhibit insulin secretion, probably by acting via $\alpha_2$ adrenergic receptors on B islet cells. Contrarily, vagal (parasympathetic) stimulation causes the release of insulin from B cells. Berger et al., *The Pancreas*, volume 1, page 110, published by Blackwell Science (1998), the entire contents of which publication (2 volumes) are incorporated herein by reference. Thus, stimulation of the dorsal vagus or the pancreatic nerve increases the output of insulin and glucagon and this response is abolished by atropine, a muscarinic acetylcholine receptor antagonist. Additionally, the parasympathetic neurotransmitter acetylcholine stimulates release of insulin from B cells in vivo and in vitro.

Thus, endocrine pancreatic activity appears to be stimulated by cholinergic fibers since, as indicated, parasympathetic innervation of islet cells can apparently increase insulin secretion, and to a lesser extent, may also increase glucagon secretion. See e.g. *Amer J. Physiol* July 1999; 277 (1 Pt 1): E93–102, *Regul Pept* Jun. 30, 1999; 82(1–3): 71–9, *J Physiol* (Lond) Mar. 1, 1999;515 (Pt 2): 463–73, *Pflugers Arch* August 1996; 432(4):589–96, and *J Surg Res* April 1990; 48(4): 273–8.

A possible physiological function of the cholinergic system in relation to insulin secretion is to contribute to the rapid insulin release seen during the cephalic phase after food intake. Significantly, B islet cells are more sensitive to cholinergic stimulation than are A islet cells, since it appears that cholinergic control is more significant over insulin secretion than it is over glucagon secretion. *J Surg Res* April 1990;48(4):273–8, at 277.

Botulinum Toxin

The anaerobic, gram positive bacterium *Clostridium botulinum* produces a potent polypeptide neurotoxin, botulinum toxin, which causes a neuroparalytic illness in humans and animals referred to as botulism. The spores of Clostridium botulinum are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unaffenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). Interestingly, on a molar basis, botulinum toxin type A is 1.8 billion times more lethal than diphtheria, 600 million times more lethal than sodium cyanide, 30 million times more lethal than cobrotoxin and 12 million times more lethal than cholera. Singh, *Critical Aspects of Bacterial Protein Toxins*, pages 63–84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

[1]Available from Allergan, Inc., of Irvine, Calif. under the tradename BOTOX® in 100 unit vials. One unit of BOTOX® contains about 50 picograms of botulinum toxin type A complex.

Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ or botulinum toxin type A. Botulinum toxin apparently binds with high affinity to cholinergic motor neurons, is translocated into the neuron and blocks the release of acetylcholine.

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months. Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Significantly, it is known that the cytosol of pancreatic islet B cells contains at least SNAP-25 (*Biochem J* 1;339 (pt 1): 159–65 (April 1999)), and synaptobrevin (*Mov Disord* May 1995; 10(3): 376).

With regard to the use of a botulinum toxin to treat a pancreatic related disorder, it is known to treat a form of pancreatitis by injecting a botulinum toxin into the minor duodenal papilla (because of the proximity of the minor papilla to the pancreatic duct) to thereby relax a constricted pancreatic duct (pancreatic divisum) and increase the flow of pancreatic juice through the pancreatic duct into the duodenum. *Gastrointest Endosc* October 1999; 50(4): 545–548.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

It has been reported that botulinum toxin type A has been used in clinical settings as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. DAS ED50 values (units/kg) were as follows: BOTOX®: 6.7, Dysport®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, Dysport®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of botulinum toxin type B. *Eur J Neurol* November 1999;6(Suppl 4):S3–S10.

Acetylcholine

Typically only a single type of small molecule neurotransmitter is released by each type of neuron in the mammalian nervous system. The neurotransmifter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetyicholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

What is needed therefore is an effective, long lasting, non-surgical resection, non-radiotherapy, non-systemic drug administration, therapeutic method for treating type 2 diabetes (NIDDM).

SUMMARY

The present invention meets this need and provides an effective, non-surgical resection, relatively long term, non-radiotherapy, non-systemic drug administration, therapeutic method for treating type 2 diabetes.

A method for treating diabetes according to the present invention can be carried out by local administration of a neurotoxin to a pancreas. The neurotoxin can be administered in an amount of between about $10^{-3}$ U/kg and about 35 U/kg. Preferably, the neurotoxin is administered in an amount of between about $10^{-2}$ U/kg and about 25 U/kg. More preferably, the neurotoxin is administered in an amount of between about $10^{-1}$ U/kg and about 15 U/kg. Most preferably, the neurotoxin is administered in an amount of between about 1 U/kg and about 10 U/kg. In many instances, an administration of from about 1 units to about 500 units of a neurotoxin, such as a botulinum toxin type A, provides effective and long lasting therapeutic relief. More preferably, from about 5 units to about 200 units of a neurotoxin, such as a botulinum toxin type A, can be used and most preferably, from about 10 units to about 100 units of a neurotoxin, such as a botulinum toxin type A, can be locally administered into a target tissue such as the pancreas or a sympathetic ganglion with efficacious results.

The neurotoxin can be made by a Clostridial bacterium, such as by a *Clostridium botulinum, Clostridium butyricum*, or *Clostridium beratti* bacterium. Additionally, the neurotoxin can be a modified neurotoxin, that is a neurotoxin that has at least one of its amino acids deleted, modified or replaced, as compared to the native or wild type neurotoxin. Furthermore, the neurotoxin can be a recombinant produced neurotoxin or a derivative or fragment thereof.

A method according to the present invention can be used to treat type 2 diabetes, such as (early) phase 1, middle or late phase type 2 diabetes. Notably, the neurotoxin, when injected into the pancreas, can act to reduce an insulin secretion and to reduce a glucagon secretion from the pancreas.

The neurotoxin can be a botulinum toxin, such as one of the botulinum toxin serotypes A, B, $C_1$, D, E, F or G. Preferably, the neurotoxin is botulinum toxin type A and the neurotoxin is locally administered by direct injection of the neurotoxin into the pancreas (when hyperinsulinemic diabetes is to be treated).

A further method within the scope of the present invention can also comprise administration of an agent for reducing insulin resistance prior to or concurrent with the local administration of the neurotoxin to the pancreas.

A detailed embodiment of a method within the scope of the present invention for treating type 2 diabetes can comprise the step of injecting a therapeutically effective amount of a botulinum toxin into a pancreas of a human patient, thereby reducing an insulin secretion from an islet B cell and treating type 2 diabetes. In this method, the type 2 diabetes is accompanied by hyperinsulinism and the insulin secretion is a cholinergic influenced insulin secretion.

Another detailed embodiment of a method within the scope of the present invention for treating type 2 diabetes of a human patient can comprise the step of local administration to a cholinergic influenced islet B cell containing, pancreatic tissue of a human patient of a therapeutically effective amount of botulinum toxin type A, thereby reducing a cholinergic influenced excessive insulin secretion from the pancreatic islet B cell and treating the type 2 diabetes.

Another method within the scope of the present invention is a method for treating excessive glucagon secretion by injecting a therapeutically effective amount of a botulinum toxin into a pancreas of a human patient, thereby reducing a glucagon secretion from an islet A cell.

A method for treating phase 2 NIDDM according to the present invention can be by injecting a therapeutically effective amount of a botulinum toxin into a pancreas of a human patient.

Another method within the scope of the present invention is a method for treating type 2 diabetes by administration of a neurotoxin to a sympathetic nervous system of a patient. In this method the neurotoxin is locally administered to a sympathetic ganglion which innervates a B cell and the type 2 diabetes is accompanied by hypoinsulinism.

A detailed embodiment of a method within the scope of the present invention for treating type 2 diabetes of a human patient can comprise the step of in vivo, local administration to a sympathetic ganglion, which innervates a pancreatic islet B cell of a patient, of a therapeutically effective amount of a botulinum toxin, thereby increasing a deficient insulin secretion from a pancreatic tissue and treating the type 2 diabetes.

The present invention therefore includes within its scope a method for treating the most prevalent form of diabetes (type 2 or NIDDM) by local administration of a neurotoxin to a pancreas or to a sympathetic ganglion thereby treating the diabetes.

A detailed embodiment of the present invention is a method for treating diabetes by injecting a therapeutically effective amount of a botulinum toxin into a pancreas of a human patient, thereby reducing a secretion from a pancreatic cell and treating the diabetes. The secretion treated can be an insulin secretion and the pancreatic disorder can be a NIDDM. Preferably, the secretion treated is a cholinergic influenced secretion and the botulinum toxin used is botulinum toxin type A, although the botulinum toxin can selected from the group consisting of botulinum toxin types A, B, C (i.e. $C_1$), D, E, F and G.

As used herein "local administration" means direct injection of the neurotoxin into the pancreas or into a sympathetic ganglion. Systemic routes of administration, such as oral and intravenous routes of administration, are excluded from the scope of the present invention.

DESCRIPTION

The present invention is based upon the discovery that diabetes, for example early phase, type 2 diabetes, can be treated by in vivo administration of a neurotoxin to the pancreas of a patient. The primary effect of the neurotoxin administered to the pancreas is to reduce the excessive insulin secretion of hyperinsulinemia. A secondary effect from administration of the neurotoxin is reduced insulin resistance.

The present invention is also based upon the discovery that diabetes, for example, middle or late phase, type 2 diabetes, can be treated by in vivo administration of a neurotoxin to a sympathetic ganglion which innervates pancreatic islet B cells of a patient. The effect of the neurotoxin administered to the sympathetic ganglion is to remove an inhibitory influence upon insulin secretion and thereby alleviate hypoinsulinemia by promoting insulin secretion.

Thus, type 2 NIDDM can be treated, according to the present invention, by the alternative therapies of (a) local administration of a neurotoxin to the pancreas or (b) local administration of a neurotoxin to a sympathetic ganglion of a patient, thereby resulting in, respectively, a reduction of a secretion from a pancreatic endocrine cell, or an increase in a secretion from a pancreatic endocrine cell.

I have discovered that a particular neurotoxin, botulinum toxin, can be used with dramatic ameliorative effect to treat type 2 diabetes, thereby significantly superseding current therapeutic regimens, such as oral insulin or sulfonylurea. Significantly, a single local pancreatic administration of a neurotoxin, such as a botulinum toxin, according to the present invention, can substantially reduce or reverse the symptoms of early phase, type 2 diabetes for at least about 2 to about 6 months. Notably, it has been reported that glandular tissue treated by a botulinum toxin can show a reduced secretory activity for as long as 27 months post injection of the toxin. *Laryngoscope* 1999; 109:1344–1346, *Laryngoscope* 1998;108:381–384. Similarly, a single local sympathetic ganglion administration of a neurotoxin, such as a botulinum toxin, according to the present invention, can substantially reduce or reverse the symptoms of middle or late phase type 2 diabetes for at least about 2–6 months. Typically, in early phase, type 2 diabetes hyperinsulinemia is present, while in middle and late phase type 2 diabetes, hypoinsulinemia has appeared.

Local Administration of a Neurotoxin to the Pancreas

A preferred embodiment of the present invention is to inject the pancreas of a patient with from 1 to 500 units, more preferably from 10 to 200 units, and most preferably from 20 to 100 units of a neurotoxin (such as a botulinum toxin type A), to thereby cause a reduction of islet cell insulin secretion. The reduction in insulin secretion is followed by a lowering of insulin resistance because insulin resistance is a reversible response to hyperinsulinemia. In a particularly, preferred embodiment of the present invention, the local administration of the neurotoxin is accompanied (with or shortly before) by administration of an agent which acts facilitates the desired reduction of insulin resistance. Suitable agents for reducing insulin resistance include thiazolidinediones, such as ciglitazone, troglitazone, pioglitazone and englitazone. These insulin resistance reducing agents can reduce blood glucose, increase the basal rate of glucose metabolism, increase lipogenesis, increase insulin receptor number and postreceptor response to insulin.

The administration of a therapeutic amount of a neurotoxin directly to the pancreas of a patient is most suited for conditions where hyperinsulinemia exists, such as early phase, type 2 (NIDDM) diabetes. The present invention also includes within its scope treatment of type 2 diabetes due to hyperplasic, hypertonic or hypertrophic B cells. The diabetes is effectively treated by local administration of a neurotoxin, such as for example 10 to 500 units of botulinum toxin type A, to cholinergic, postganglionic, parasympathetic neurons which innervate the dysfunctional, hypersecretory B cells. Without wishing to be bound by theory, the botulinum toxin is believed to act by inhibiting release of acetylcholine neurotransmitter from cholinergic, postganglionic parasympathetic fibers which innervate pancreatic islet B cells.

A neurotoxin, such as a botulinum toxin, locally administered in vivo to the pancreas reduces a secretory activity of an islet secretory cell. With this approach the target tissue is cholinergically innervated or susceptible to high toxin dosing such that the proteolytic light chain of the toxin is internalized by a cholinergic neuron which influences a secretory activity of a pancreatic islet cell.

Thus, cholinergically innervated pancreatic islet cells can be treated by local administration of a neurotoxin, such as a botulinum toxin. By local administration it is meant that the neurotoxin is administered directly to or to the immediate vicinity of the pancreatic islet tissue to be treated.

The specific dosage appropriate for administration is readily determined by one of ordinary skill in the art according to the factor discussed above. The dosage can also depend upon the size of the pancreatic tissue mass to be treated or denervated, and the commercial preparation of the toxin. Additionally, the estimates for appropriate dosages in humans can be extrapolated from determinations of the amounts of botulinum required for effective denervation of other tissues. Thus, the amount of botulinum A to be injected is proportional to the mass and level of activity of the pancreatic tissue to be treated. Generally, between about 0.01 and 35 units per kg of patient weight of a botulinum toxin, such as botulinum toxin type A, can be administered to effectively accomplish a toxin induced pancreatic endocrine tissue secretion down regulation upon administration of the neurotoxin into the pancreas. Less than about 0.01 U/kg of a botulinum toxin does not have a significant therapeutic effect upon the secretory activity of a pancreatic cell, while more than about 35 U/kg of a botulinum toxin approaches a toxic dose the neurotoxin. Careful placement of the injection needle and a low volume of neurotoxin used prevents significant amounts of botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the pancreatic tissue to be treated and the administration route chosen. Botulinum toxin type A is a preferred botulinum toxin serotype for use in the methods of the present invention.

It has been reported that the neuronal selectivity of clostridial neurotoxins is a result of a very selective binding and cell entry mechanism. Although a site of action of botulinum toxin is the neuromuscular junction, where the toxin binds rapidly and prevents the release of acetylcholine from cholinergic neurons, it is known that clostridial neurotoxins are able to enter certain neurosecretory cells (for example PC12 cells) via a low affinity receptor if high concentrations of the neurotoxin are incubated with the cells for prolonged periods. This process appears to use a pathway via a receptor which is distinct from the highly specific and high affinity receptor present at the neuromuscular junction. Additionally, it has been reported that certain clostridial toxins have effects on phagocyte cells, such as macrophages, where entry into the cell is presumed to be via the specific phagocytic activity of these cells. Furthermore, incubation of certain adipocytes (i.e. fat cells) with botulinum toxin type A has been reported to inhibit glucose uptake by the adipocytes. The mechanism of the glucose uptake s inhibition is apparently due to toxin inhibition of plasma membrane fusion or docking of cytosolic, recyclable membrane vesicles (RMVs), the RMVs containing glucose transporter proteins. PCT publication WO 94/21300.

Thus, while it is known that the botulinum toxins have a known binding affinity for cholinergic, pre-synaptic, peripheral motor neurons, it has been reported that botulinum toxins can also bind to and translocate into a variety of non-neuronal secretory cells, where the toxin then acts, in the known manner, as an endoprotease upon its respective secretory vessel-membrane docking protein. Because of the relatively lower affinity of the botulinum toxins for secretory cells, such as pancreatic cells, as compared to the affinity of the botulinum toxin for the cholinergic neurons which innervate pancreatic cells, the botulinum toxin can be injected into secretory or glandular tissues to provide a high local concentration of the toxin, thereby facilitating effect of the toxin upon both cholinergic neuron and directly upon pancreatic secretory cell. Thus, the present invention is applicable to the treatment of pancreatic disorders wherein the target endocrine pancreatic cells have little or no cholinergic innervation.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known safe and efficacious use for the treatment of skeletal muscle and smooth muscle disorders when locally administered by intramuscular injection.

The present invention includes within its scope the use of any neurotoxin which has a long duration therapeutic effect when locally applied to treat a pancreatic islet cell disorder of a patient. For example, neurotoxins made by any of the species of the toxin producing Clostridium bacteria, such as *Clostridium botulinum*, *Clostridium butyricum*, and *Clostridium beratti* can be used or adapted for use in the methods of the present invention. Additionally, all of the botulinum serotypes A, B, C, D, E, F and G can be advantageously used in the practice of the present invention, although type A is the most preferred serotype, as explained above. Practice of the present invention can provide effective relief of diabetes for from 2–27 months or longer in humans.

It is known that release of insulin from permeabilized (as by electroporation) insulin secreting cells can be inhibited by a botulinum toxin. When in vitro, the cell membranes of these non-nerve cells can be permeabilized to assist introduction of a botulinum toxin into the cell's cytosol due to the lack of cell surface receptors for a botulinum toxin. Thus, botulinum toxin type B apparently inhibits insulin secretion by cleaving synaptobrevin present in the insulin secreting cell line HIT-15. Boyd R. S., et al *The Effect of Botulinum Neurotoxin-B On Insulin Release From a Beta Cell*, Mov Disord 10(3):376 (1995). Thus, it may be that a botulinum toxin can block the release of any vesicle mediated exocytosis from any secretory (i.e. neuronal, glandular, secretory, chromaffin) cell type, as long as the light chain of the botulinum toxin is translocated into the intracellular medium. For example, the intracellular protein SNAP-25 is widely distributed in both neuronal and non-neuronal secretory cells and botulinum toxin type A is an endopeptidase for which the specific substrate is SNAP-25. Thus, while cholinergic neurons have a high affinity acceptor for the botulinum and tetanus toxins (and are therefore more sensitive than other neurons and other cells to the inhibition of vesicle mediated exocytosis of secretory compounds), as the toxin concentration is raised, non-cholinergic sympathetic neurons, chromaffin cells and other cell types can take up a botulinum toxin and show reduced exocytosis.

Hence, by practice of the present disclosed invention, non-cholinergic nerve fibers as well as non or poorly innervated pancreatic endocrine cells can be treated by use of an appropriately higher concentration of a botulinum toxin to bring about therapeutic relief from diabetic hyperinsulinemia, as the secondary disorder insulin resistance.

Local Administration of a Neurotoxin to a Sympathetic Ganglion

Significantly, a method within the scope of the present invention for increasing a deficient insulin secretion comprises the step of local administration of a neurotoxin to the sympathetic nervous system. Sympathetic innervation of the endocrine pancreas is know to exist. Thus, sympathetic nerve fibers can inhibit insulin secretion by acting via $\alpha_2$ adrenergic receptors on B islet cells. A method within the scope of the present invention can therefore be carried out by local administration of a neurotoxin to a cholinergic, preganglionic sympathetic neuron. The cholinergic, preganglionic, sympathetic neurons synapse with adrenergic, postganglionic, sympathetic fibers, and these later sympathetic neurons have an inhibitory effect upon insulin secretion by pancreatic islet B cells.

The celiac ganglia are the largest and highest group of prevertebral sympathetic ganglia, located on the superior part of the abdominal aorta, on either side of the origin of the celiac artery. The celiac ganglia lie within the celiac plexus and comprise cholinergic, sympathetic preganglionic fibers which synapse with adrenergic, sympathetic, postganglionic nerves. The celiac ganglia innervates the dorsal pancreas, while the superior mesenteric ganglia innervates the ventral pancreas. Celiac ganglion block according to the present invention can be carried out in the same manner as a celiac plexus block.

Thus, the neurolytic celiac plexus block is a known procedure for treating intractable pain resulting from upper abdominal viscera cancer. *Reg Anest Pain Med* 1998; 23(1):37–48. The celiac plexus contains both afferent and efferent visceral fibers, with minor vagal nerve contribution. *Anest* 1997;87(6):1301–1308. Thus, it is known to inject the celiac plexus with ethanol or phenol to provide relief from the pain which can result from pancreatic cancer or from pancreatitis. *AJG* 1999;94(4):872–874. The antinociceptive injection can be carried out as by either a percutaneous procedure or as an open (intraoperative) injection. The percutaneous (closed) procedure can be carried out using an anterior approach using a very thin needle (22 Gauge). Celiac plexus block is preferably carried out with computed tomography (CT) (as opposed to fluoroscopic) needle guidance (*Reg Anest Pain Med* 1999;24(5);483–484) and can be carried out with the needle tip positioned anterior to aorta. The procedure can be performed with anterior approach, the patient being in a supine position, using a single thin needle.

A preferred method within the scope of the present invention for increasing insulin secretion by removing sympathetic inhibition upon B cells can be carried out by local administration of a neurotoxin to either or both of the celiac ganglia and/or to the superior mesenteric ganglia.

Furthermore, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, I have discovered that a surprisingly effective and long lasting therapeutic effect can be achieved by local administration of a neurotoxin to the pancreas or to a sympathetic ganglion which innervates the pancreas of a human patient. In its most preferred embodiment, the present invention is practiced by direct injection into the pancreas or into the sympathetic ganglion of botulinum toxin type A. It has been reported that at the neuroglandular junction, the chemical denervation effect of a botulinum toxin, such as botulinum toxin type A, has a long duration of action, i.e. 27 months vs. 3 months.

Without wishing to be bound by theory, applicant postulates that the hyperinsulinism of type 2 diabetes arises first followed by insulin resistance as an ensuing protective response. An appropriate therapeutic goal when hyperinsulinemia is present is therefore to reduce the excessive B cell insulin secretion (and co-existing excess A cell glucagon secretion) to permit insulin resistance to reverse. Thus, appropriate therapy for at least phase 1, type 2 NIDDM may be directed to reducing or inhibiting the excessive insulin secretion. Hyperglycemia does not result upon therapeutic administration apparently because upon local pancreatic administration of a neurotoxin, as disclosed herein, the reduced insulin secretion is followed by a concomitant reduction in the insulin resistance and improved glucose utilization.

Thus, it can be reasonably postulated that hypersecretion of insulin is the initial lesion in the pathogenesis of type 2 diabetes and that this primary lesion is the result of an excessive cholinergic stimulation of the B cells (see e.g. *Pflugers Arch, Eur J Physiol* (1996) 432: 589–596, at 595). Insulin resistance therefore becomes a secondary effect and a protective result of the initial lesion hyperinsulinemia. The immediate cause of insulin resistance in type 2 diabetes is believed to be due not to insulin receptor binding problems but from post binding abnormalities. Thus, hyperinsulinemia causes down regulation of the number of insulin receptors and leads to post-insulin binding to receptor defects. *Medical Management of Type 2 Diabetes*, edited by David Kelley, published by the American Diabetes Association, fourth edition, page 25 (1998), the entire contents of which publication are incorporated herein by reference.

It has been reported that the B islet cells show increased sensitivity to cholinergic stimulation when insulin resistance is present. *Amer J. Physiol*, July 1999; 277 (1 Pt 1):E93–102. Additionally, it is believed that cholinergic stimulation of B cells has profound effects on B cell sensitivity to glucose and that the stimulatory effect of vagally released acetylcholine is a prime causative IS factor in the development of hyperinsulinemia and insulin resistance. *Pflugers Arch, Eur J Physiol* (1996) 432: 589–596. Importantly, I have discovered that down regulation of B cell activity, by the invention disclosed herein, can importantly reduce not only the hypersecretion of insulin and resulting hyperinsulinemia, but also permits insulin resistance to subside with concomitant reduced sensitivity of B cells to cholinergic stimulation.

Furthermore, it is believed that in response to hyperinsulinemia, the overall insulin receptor numbers are reduced on the insulin target tissues (*Type 2 Diabetes Prediction and Prevention*, edited by Hitman, page 199, supra) and it is therefore reasonable to conclude that a reduction in the level of insulin secretion by the B cells, will permit a concomitant rise in the number of insulin receptors, with resulting higher glucose utilization.

Thus, it is the inventor's premise that stimulation of B cells, in an attempt to overcome insulin resistance, is an inappropriate therapeutic methodology for treating early phase type 2 diabetes, because insulin resistance is merely the result of the primary and prior arising hyperinsulin secretion. The appropriate therapeutic methodology, as set forth herein, is to treat the causative factor (B cell dysfunction) not the resulting symptom (insulin resistance). Carbachol causes an acute stimulation of insulin release, while prolonged exposure to carbachol actually suppresses insulin release. *Pflugers Arch, Eur J Physiol* (1996) 432: 589–596, at 594.

Hence, the therapeutic efficacy of administration of carbachol or similar apparent cholinergic agonist, to treat the chronic hyperinsulinism of type 2 diabetes appears to reside in a long term reduction in the level of excessive insulin secretion by the B cells. The applicant's proposed mechanism for the efficacy of local administration of a neurotoxin, such as a botulinum toxin, to treat the chronic hyperinsulinism of type 2 diabetes (i.e. long duration reduction of B cell cholinergic stimulation) appears to be supported by the mechanism by which at least the cholinergic agonist carbachol alleviates insulin resistance—by reducing long term insulin secretion to thereby permit the coexisting insulin resistance to subside.

The present invention includes within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for a cell surface receptor present on an endocrine pancreatic cell.

Botulinum toxins for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

The route of administration and amount of a neurotoxin (such as a botulinum toxin serotype A, B, C, D, E, F or G) administered according to the present invention for treating diabetes can vary widely according to various patient variables including size, weight, age, disease severity, responsiveness to therapy, and solubility and diffusion characteristics of the neurotoxin toxin chosen. Furthermore, the extent of the pancreatic or ganglionic tissue influenced is believed to be proportional to the volume of neurotoxin injected, while the quantity of the denervation is, for most dose ranges, believed to be proportional to the concentration of neurotoxin injected.

Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, to treat early phase, type 2 diabetes, a solution of botulinum toxin type A complex can be endoscopically or intraperitoneally injected directly into the tissues of the pancreas, thereby substantially avoiding entry of the toxin into the systemic circulation.

EXAMPLES

The following examples provide those of ordinary skill in the art with specific preferred methods within the scope of the present invention for carrying out the present invention and are not intended to limit the scope of what the inventor regards as his invention.

Example 1

Local Administration of a Neurotoxin to the Endocrine Pancreas

Local administration of a neurotoxin directly to or to the vicinity of pancreatic endocrine cells can be accomplished by several methods. For example, pancreatic endoscopy for diagnostic and therapeutic purposes is well known. Therapeutic pancreatic endoscopic techniques include pancreatic sphincterotomy, stricture dilation, stenting, pseudocyst drainage and endoscopic retrograde cholangiopancreatography (ERCP) which permits visualation of and treatment of the pancreatic-biliary ductal system. An endoscope used for pancreatic therapy can be modified to permit its use for direct injection of a neurotoxin, such as a botulinum toxin directly into pancreatic tissue. See for example U.S. Pat. No. 5,674,205. For the purposes of the present invention, the endoscope is moved from the oropharynx through the stomach, duodenum, and finally into the pancreatic duct, duct decompression having been carried out previously (for example by dilation or stenting), if required, to permit lodgment of the endoscope in the duct. Once so located, a hollow needle tip can be extended from the endoscope into pancreatic tissue and through which needle the neurotoxin can be injected into the pancreatic tissue.

If the pancreatic duct is not accessible or does not decompress, a percutaneous needle, imaging guided (i.e. by ultrasound or computed tomography) can also be used for transabdominal injection of a neurotoxin directly into pancreatic tissue. Thus, percutaneous needle aspiration for pancreatic biopsy is a known technique and aspiration can be reversed to accomplish the desired toxin injection.

In each of the following examples, the specific amount of a botulinum toxin administered depends upon a variety of factors to be weighed and considered within the discretion of the attending physician and in each of the examples insignificant amounts of botulinum toxin enter appear systemically with no significant side effects. Units of botulinum toxin injected per kilogram (U/kg) below are per kg of total patient weight. For example, 3 U/kg for a 70 kg patient calls for an injection of 210 units of the botulinum toxin.

Example 2

Treatment of Type 2 Diabetes with Botulinum Toxin Type A

A 48 year old obese male is diagnosed with early phase, type 2 diabetes (NIDDM). Between about $10^{-3}$ U/kg and about 35 U/kg of a botulinum toxin type A preparation (for example between about 10 units and about 500 units of BOTOX®) is injected directly into the pancreas, using one of the techniques set forth in Example 1. Within 1–7 days the symptoms of diabetes are alleviated. Insulin levels return to normal without hyperglycemia. Alleviation of the diabetes persists for at least about 2 months to about 6 months.

Example 3

Treatment of Type 2 Diabetes with Botulinum Toxin Type B

A 48 year old obese male is diagnosed with early phase, type 2 diabetes (NIDDM). Between about $10^{-3}$ U/kg and about 35 U/kg of a botulinum toxin type B, preparation (for example, between about 1000 units and about 20,000 units of a botulinum type B preparation) is injected directly into the pancreas, using one of the techniques set forth in Example 1. Within 1–7 days the symptoms of diabetes are alleviated. Insulin levels return to normal without hyperglycemia. Alleviation of the diabetes persists for at least 2–6 months.

Example 4

Treatment of Type 2 Diabetes with Botulinum Toxin Type C

A 48 year old obese male is diagnosed with early phase, type 2 diabetes (NIDDM). Between about 10 units and about 10,000 units of a botulinum type C, preparation is injected directly into the pancreas, using one of the techniques set forth in Example 1. Within 1–7 days the symptoms of diabetes are alleviated. Insulin levels return to normal without hyperglycemia. Alleviation of the diabetes persists for at least 2–6 months.

Example 5

Treatment of Type 2 Diabetes with Botulinum Toxin Type D

A 48 year old obese male is diagnosed with early phase, type 2 diabetes (NIDDM). Between about 10 units and about 10,000 units of a botulinum type D preparation is injected directly into the pancreas, using one of the techniques set forth in Example 1. Within 1–7 days the symptoms of diabetes are alleviated. Insulin levels return to normal without hyperglycemia. Alleviation of the diabetes persists for at least 2–6 months.

Example 6

Treatment of Type 2 Diabetes with Botulinum Toxin Type E

A 48 year old obese male is diagnosed with early phase, type 2 diabetes (NIDDM). Between about 10 units and about 10,000 units of a botulinum type E preparation is injected directly into the pancreas, using one of the techniques set forth in Example 1. Within 1–7 days the symptoms of diabetes are alleviated. Insulin levels return to normal without hyperglycemia. Alleviation of the diabetes persists for at least 2–6 months.

Example 7

Treatment of Type 2 Diabetes with Botulinum Toxin Type F

A 48 year old obese male is diagnosed with early phase, type 2 diabetes (NIDDM). Between about 10 units and about 10,000 units of a botulinum type F preparation is injected directly into the pancreas, using one of the techniques set forth in Example 1. Within 1–7 days the symptoms of diabetes are alleviated. Insulin levels return to normal without hyperglycemia. Alleviation of the diabetes persists for at least 2–6 months.

Example 8

Treatment of Type 2 Diabetes with Botulinum Toxin Type G

A 48 year old obese male is diagnosed with early phase, type 2 diabetes (NIDDM). Between about 10 units and about 10,000 units of a botulinum type G preparation is injected directly into the pancreas, using one of the techniques set forth in Example 1. Within 1–7 days the symptoms of diabetes are alleviated. Insulin levels return to normal without hyperglycemia. Alleviation of the diabetes persists for at least 2–6 months.

Example 9

Two Step Method for Treatment of Diabetes with Botulinum Toxin Type A

A 34 year old female is diagnosed with early phase, type 2 diabetes (NIDDM). Between about 10 units and about 500 units of a botulinum toxin type A preparation (i.e. BOTOX®) is injected into the patients pancreas, using one of the techniques set forth in Example 1. Prior to or concurrent with the botulinum toxin injection a therapeutic dose of a thiazolidinedione is administered to reduce insulin resistance. Within 1–7 days the symptoms of diabetes are alleviated. Insulin levels return to normal without hyperglycemia. Alleviation of the diabetes persists for at least 2–6 months.

Example 10

Two Step Method for Treatment of Diabetes with Botulinum Toxin Types B–G

A 34 year old female is diagnosed with early phase, type 2 diabetes (NIDDM). Between about 10 units and about 10,000 units of a botulinum toxin of one of the serotypes B, C, D, E, F or G is injected into the patients pancreas, using one of the techniques set forth in Example 1. Prior to or concurrent with the botulinum toxin injection a therapeutic dose of a thiazolidinedione is administered to reduce insulin resistance. Within 1–7 days the symptoms of diabetes are alleviated. Insulin levels return to normal without hyperglycemia. Alleviation of the diabetes persists for at least 2–6 months.

Example 11

Treatment of Type 2 Diabetes with Botulinum Toxin Type A

A 53 year old male is diagnosed with middle or late phase type 2 diabetes (NIDDM). Between about $10^{-3}$ U/kg and about 35 U/kg of a botulinum toxin type A preparation (for example between about 10 units and about 500 units of BOTOX®) is injected directly into the celiac ganglia as follows. A percutaneous procedure is carried out using an anterior approach with the patient in a supine position using a very thin needle (22 Gauge) with computed tomography needle guidance to reach the celiac ganglia. Within 1–7 days the symptoms of diabetes are alleviated. Insulin levels return to normal (are raised) without hypoglycemia. Alleviation of the diabetes persists for at least 2–6 months.

Methods according to the invention disclosed herein has many advantages, including the following:

(1) the invention renders unnecessary many surgical procedures for effective treatment of type 2 diabetes.

(2) systemic drug effects can be avoided by direct local application of a neurotoxin according to the present invention.

(3) the ameliorative effects of the present invention can persists, on average, from 2–6 months from a single local administration of a neurotoxin as set forth herein.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local pancreatic administration methods wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type E. Alternately, a combination of any two or more of the botulinum serotypes A–G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

My invention also includes within its scope the use of a neurotoxin, such as a botulinum toxin, in the preparation of a medicament for the treatment of diabetes by local administration of the neurotoxin.

Accordingly, the spirit and scope of the following claims should not be limited to the descriptions of the preferred embodiments set forth above.

I claim:

1. A method for treating diabetes, the method comprising the step of local administration of a neurotoxin to a cholinergically innervated pancreatic cell, thereby treating diabetes.

2. The method of claim 1, wherein the neurotoxin is administered in an amount of between about $10^{-3}$ U/kg and about 35 U/kg.

3. The method of claim 2, wherein the neurotoxin is administered in an amount of between about $10^{-2}$ U/kg and about 25 U/kg.

4. The method of claim 3, wherein the neurotoxin is administered in an amount of between about $10^{-2}$ U/kg and about 15 U/kg.

5. The method of claim 4, wherein the neurotoxin is administered in an amount of between about 1 U/kg and about 10 U/kg.

6. The method of claim 1, wherein the neurotoxin is made by a Clostridial bacterium.

7. The method of claim 1, wherein the neurotoxin is made by a bacterium selected from the group consisting of *Clostridium botulinum, Clostridium butyricum*, and *Clostridium beratti.*

8. The method of claim 1, wherein the neurotoxin is a modified neurotoxin.

9. The method of claim 1, wherein the neurotoxin has at least one of its amino acids deleted, modified or replaced, as compared to a native neurotoxin.

10. The method of claim 1, wherein the neurotoxin is a recombinant produced neurotoxin or a derivative or fragment thereof.

11. The method of claim 1, wherein the diabetes is type 2 diabetes.

12. The method of claim 11, wherein the diabetes is a phase 1, type 2 diabetes.

13. The method of claim 11, wherein the neurotoxin acts to reduce an insulin secretion from the pancreas.

14. The method of claim 11, wherein the nourotoxin acts to reduce a glucagon secretion from the pancreas.

15. The method of claim 1, wherein the neurotoxin is locally administered by direct injection of the neurotoxin into the pancreas.

16. The method of claim 1, further comprising administration of an agent for reducing insulin resistance prior to or concurrent with the local administration of the neurotoxin to the pancreas.

17. A method for treating type 2 diabetes, the method comprising the step of local administration of a therapeutically effective amount of a neurotoxin into a cholinergically innervated pancreatic cell of a human patient, thereby reducing an insulin secretion from an Islet B cell and treating type 2 diabetes.

18. The method of claim 17, wherein the type 2 diabetes is accompanied by hyperinsulinism.

19. A method for treating type 2 diabetes of a human patient, the method comprising the step of local administration to a cholinergic influenced Islet B cell containing, pancreatic tissue of a human patient of a therapeutically effective amount of neurotoxin , thereby reducing a cholinergic influenced excessive insulin secretion from the pancreatic tissue and treating the type 2 diabetes.

20. A method for treating excessive glucagon secretion, the method comprising the step of local administration of a therapeutically effective amount of a nourotoxin to a cholinergically innervated pancreatic cell of a human patient, thereby reducing a glucagon secretion from an Islet A cell.

21. A method for treating phase 2 NIDDM, the method comprising the step of injecting a therapeutically effective amount of a neurotoxin to a cholinergically innervated pancreatic cell of a human patient, thereby treating phase 2 NIDDM.

22. A method for treating type 2 diabetes, the method comprising the step of administration of a neurotoxin to a cholinergic sympathetic nervous system of a patient.

23. The method of claim 22, wherein the neurotoxin is locally administered to a sympathetic ganglion which innervates a B cell.

24. The method of claim 22, wherein the type 2 diabetes is accompanied by hypoinsulinism.

25. A method for treating type 2 diabetes of a human patient, the method comprising the step of in vivo, local administration to a cholinergic sympathetic ganglion, which innervates a pancreatic islet B cell of a patient, of a therapeutically effective amount of a neurotoxin, thereby increasing a deficient insulin secretion from the pancreatic islet B cell and treating the type 2 diabetes.

* * * * *